US012076357B2

(12) United States Patent
Herbeaux et al.

(10) Patent No.: US 12,076,357 B2
(45) Date of Patent: Sep. 3, 2024

(54) PREPARATIONS CONTAINING BERRY EXTRACTS FOR USE IN THE PROPHYLAXIS AND/OR TREATMENT OF VIRAL INFECTIONS CAUSED BY PARAMYXOVIRIDAE

(71) Applicant: Evonik Operations GmbH, Essen (DE)

(72) Inventors: Jean-Luc Herbeaux, Cascais (PT); Norbert Windhab, Hofheim (DE); Anne Benedikt, Frankfurt (DE); Andrea Engel, Birmingham, AL (US); Maria Steinke, Höchberg (DE); Jochen Bodem, Geroldshausen (DE)

(73) Assignee: Evonik Operations GmbH, Essen (DE)

( * ) Notice: Subject to any disclaimer, the term of this patent is extended or adjusted under 35 U.S.C. 154(b) by 450 days.

(21) Appl. No.: 17/598,487

(22) PCT Filed: Mar. 27, 2020

(86) PCT No.: PCT/EP2020/058642
§ 371 (c)(1),
(2) Date: Sep. 27, 2021

(87) PCT Pub. No.: WO2020/201042
PCT Pub. Date: Oct. 8, 2020

(65) Prior Publication Data

US 2022/0184163 A1 Jun. 16, 2022

(30) Foreign Application Priority Data

Mar. 29, 2019 (EP) .................................... 19166036
Mar. 29, 2019 (EP) .................................... 19166060

(51) Int. Cl.
*A61K 36/45* (2006.01)
*A61K 9/00* (2006.01)
(Continued)

(52) U.S. Cl.
CPC ............ *A61K 36/45* (2013.01); *A61K 9/0014* (2013.01); *A61K 9/0019* (2013.01);
(Continued)

(58) Field of Classification Search
CPC .... A61K 36/45; A61K 9/0014; A61K 9/0019; A61K 9/0078; A61K 9/0095;
(Continued)

(56) References Cited

U.S. PATENT DOCUMENTS 9,168,276 B2 10/2015 Bombardelli et al.
2009/0220594 A1 9/2009 Field
2014/0037727 A1 2/2014 Field

FOREIGN PATENT DOCUMENTS

CN 108185010 A 6/2018
GB 2562260 A 11/2018
(Continued)

OTHER PUBLICATIONS

Evonik, Evonik launches its new PQQ product PentaQQ, Nov. 18, 2016, Evonix, pp. 1-2. (Year: 2016).*
(Continued)

*Primary Examiner* — Trevor Love
(74) *Attorney, Agent, or Firm* — Oblon, McClelland, Maier & Neustadt, L.L.P.

(57) ABSTRACT

A composition may be used in treating or preventing a virus infection in a subject, wherein the virus is from the Paramyxoviridae family and wherein the composition includes an extract of black currants and bilberries. The composition may contain an extract from black currants and bilberries in a weight ratio in a range of from 0.5:1 to 1:0.5.
(Continued)

Influence of Healthberry® 865 on the viability of Vero Slam cells. The increase of luciferase activity, measured at nine different time-points, was normalized to the increase of control cells incubated with the medium. Error bars represent the standard deviation.

The extract may be an alcoholic extract, such as a methanol extract. The composition may be administered to the subject 1 to 10 oral dosages of at least 80 mg anthocyanins each per day, preferably 3 to 6 oral dosages of at least 80 mg anthocyanins each per day. The subject may not have received a measles vaccination or have previously been exposed to the measles virus.

13 Claims, 11 Drawing Sheets

(51) Int. Cl.
*A61K 31/7048* (2006.01)
*A61K 36/185* (2006.01)
*A61K 45/06* (2006.01)
*A61P 31/14* (2006.01)

(52) U.S. Cl.
CPC .......... *A61K 9/0078* (2013.01); *A61K 9/0095* (2013.01); *A61K 31/7048* (2013.01); *A61K 36/185* (2013.01); *A61K 45/06* (2013.01); *A61P 31/14* (2018.01); *A61K 2236/333* (2013.01); *A61K 2236/51* (2013.01); *A61K 2236/53* (2013.01)

(58) Field of Classification Search
CPC .. A61K 31/7048; A61K 36/185; A61K 45/06; A61K 2236/333; A61K 2236/51; A61K 2236/53; A61P 31/14
See application file for complete search history.

(56) References Cited

FOREIGN PATENT DOCUMENTS

| | | | |
|---|---|---|---|
| WO | WO 97/41137 | A1 | 11/1997 |
| WO | WO 03/039569 | A1 | 5/2003 |

OTHER PUBLICATIONS

U.S. Appl. No. 17/598,647, filed Sep. 27, 2021, Herbeaux, et al.
U.S. Appl. No. 17/598,557, filed Sep. 27, 2021, Herbeaux, et al.
U.S. Appl. No. 17/598,587, filed Sep. 27, 2021, Herbeaux, et al.
International Search Report and Written Opinion issued on Jul. 16, 2020 in PCT/EP2020/058642 filed Mar. 27, 2020, 4 pages.
Ikuta, K., et al., "Anti-viral and anti-bacterial activities of an extract of blackcurrants (*Ribes nigrum* L.)", Microbiology and Immunology, vol. 56, XP009516099, 2012, pp. 805-809.
"Nasal Spray", Mintel, XP002757968, 2009, 4 total pages.

* cited by examiner

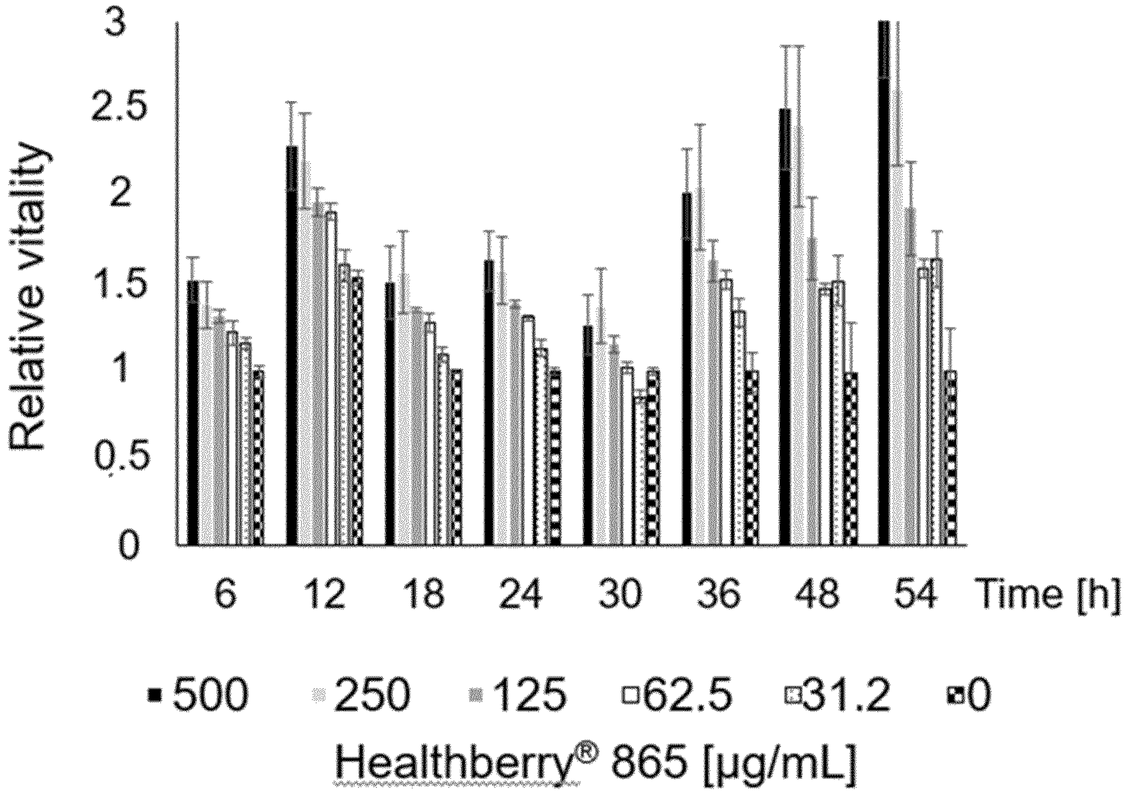
Figure 1: Influence of Healthberry® 865 on the viability of Vero Slam cells. The increase of luciferase activity, measured at nine different time-points, was normalized to the increase of control cells incubated with the medium. Error bars represent the standard deviation.

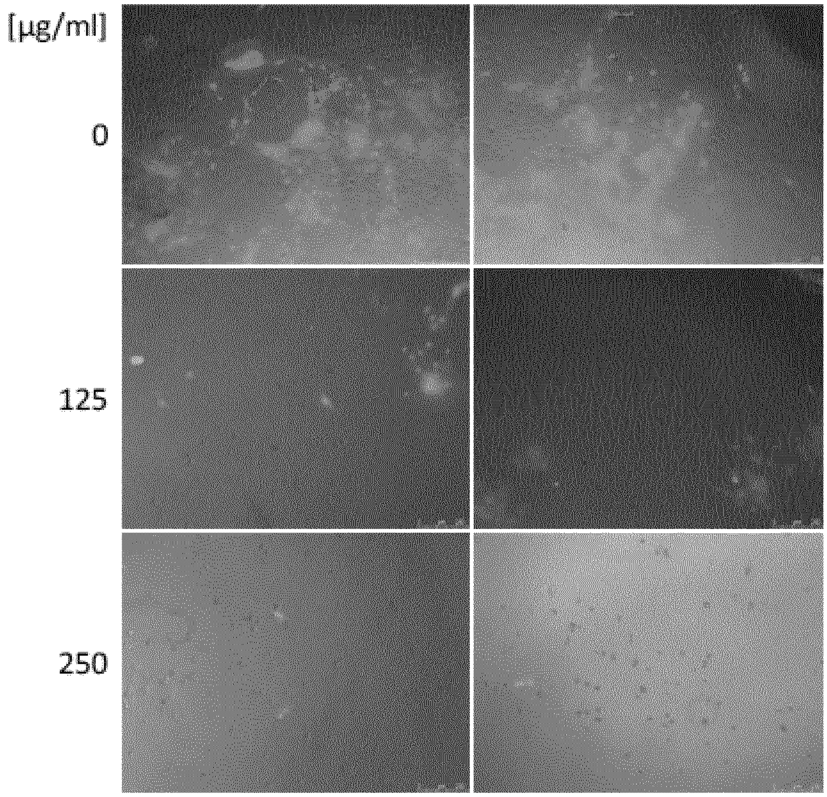
Figure 2: Healthberry® 865 inhibits measles virus infection (pictures for Healthberry® 865 concentration of 125 and 250 µg/mL). Vero-Slam cells were infected with GFP-encoding measles virus in the presence of the compound. Infected cells were visualized by fluorescence microscopy.

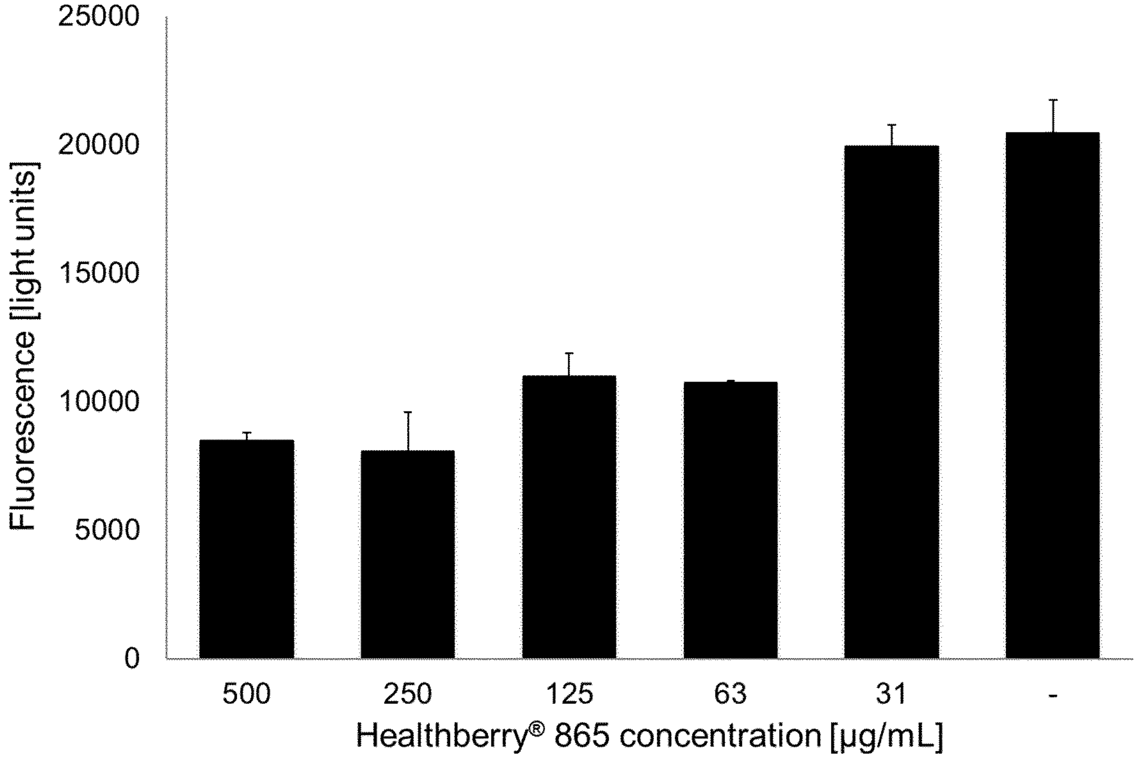
Figure 3: Determination of the inhibition of viral infections by different concentrations of Healthberry® 865. Vero-Slam cells were infected with GFP-encoding measles virus. Fluorescence was measured, each bar represents the mean of 3 independent infections. Error bars the standard deviation.

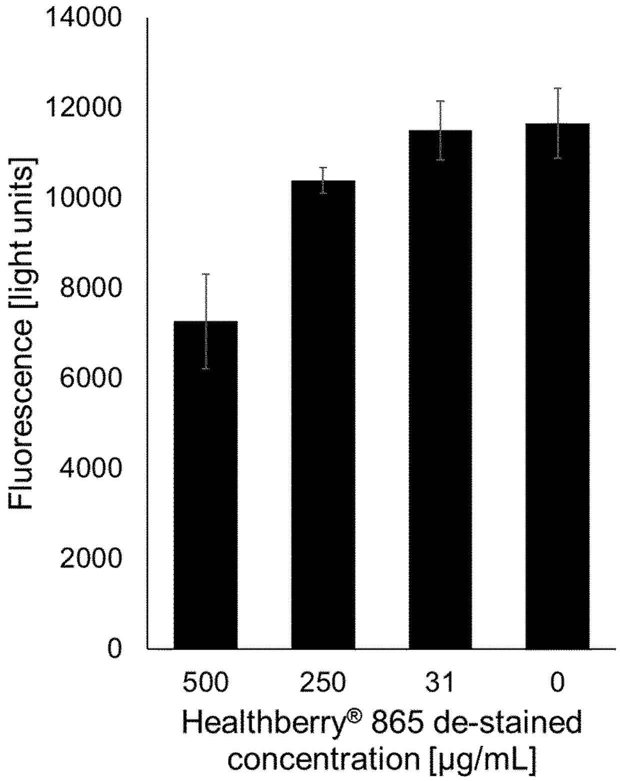
Figure 4: Inhibition of viral replication by de-stained version of Healthberry® 865. Vero-Slam cells were infected with GFP-encoding measles virus. Fluorescence was measured, and each value represents the mean of three independent infections. Error bars represent the standard deviation.

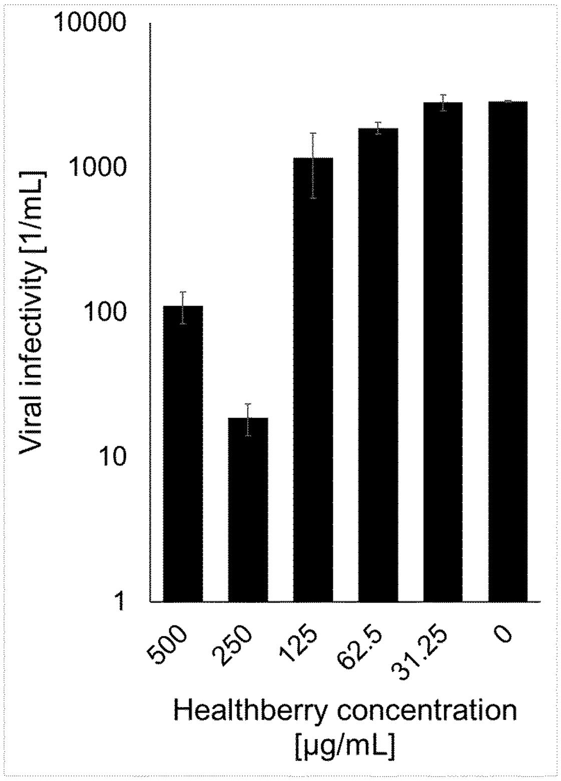
Figure 5: Healthberry® 865 reduces measles virus infection of Vero Slam cells significantly (log scale). Vero cells were infected with GFP-encoding measles virus in triplicates and GFP expressing cells were counted using the Ensight system. Error bars indicate the standard deviation of three independent samples.

Figure 6: D3R influences viral replication (log scale). A: D3G, B: D3R, C:C3G, D: C3R, E: mixture of D3G/D3R/C3G/C3R. Cells were infected with GFP-encoding measles virus in quadruplets. Infected cells were counted with the PerkinElmer Ensight system. Error bars indicate the standard deviation of four independent samples.

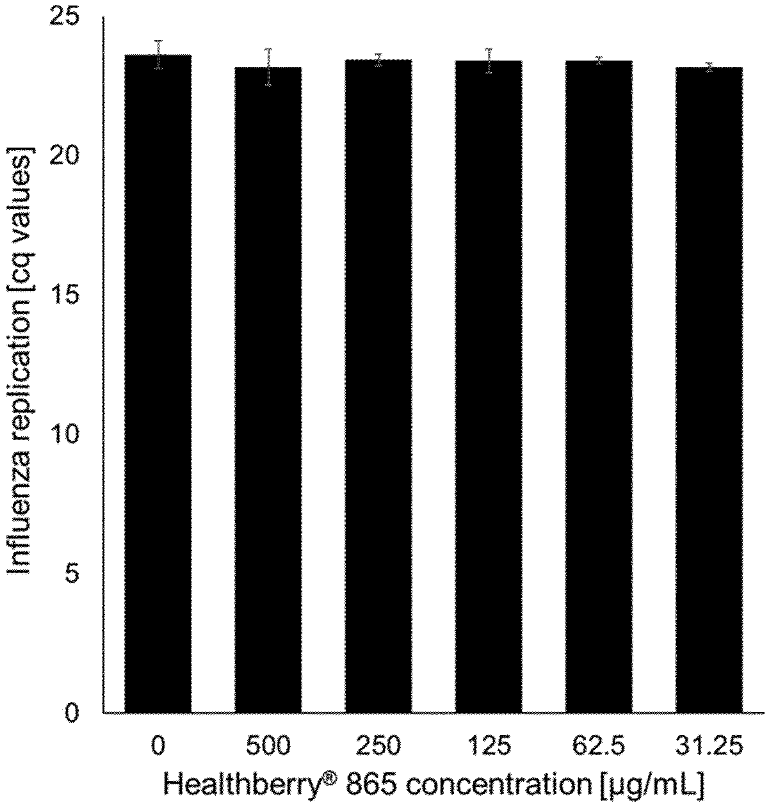
Figure 7: Replication of influenza virus is not influenced by Healthberry® 865. MDCK cells were pretreated with Healthberry® 865, infected with influenza virus (serotype A). Viral RNAs were isolated and quantified by RTqPCR (Cq-values). Note: lower Cq values correspond to higher viral loads.

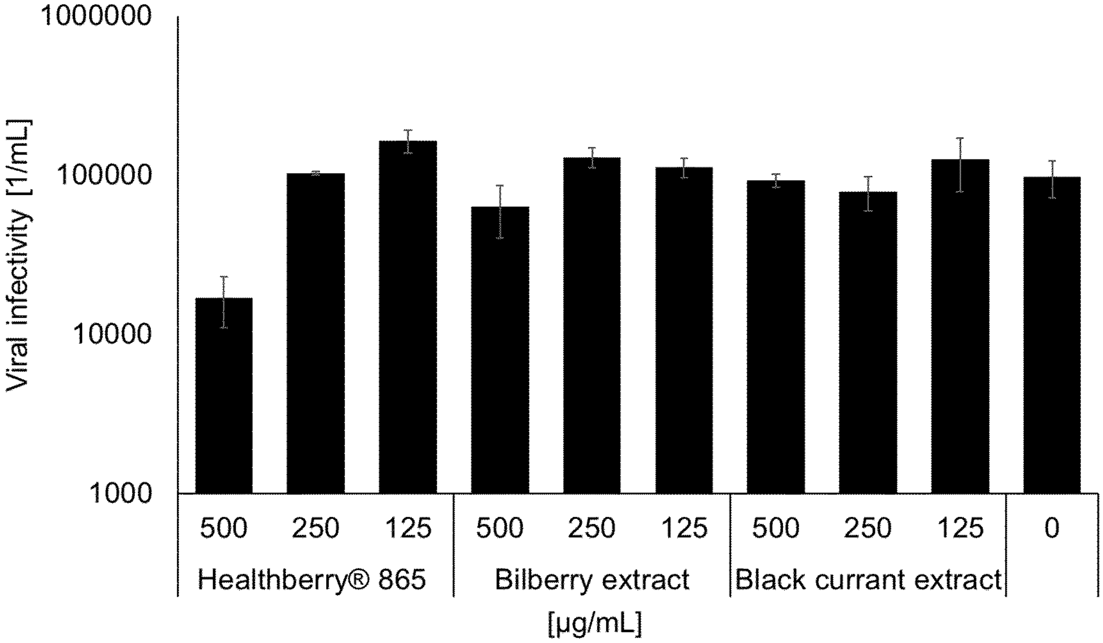

Figure 8: Neither Bilberry nor Black currant extract reduces measles virus infections of Vero Slam cells in contrast to Healthberry® 865 (log scale). Vero-Slam cells were incubated with HB, Bilberry, or Black currant extracts and subsequently infected with GFP-encoding measles viruses. Cells expressing GFP were counted 2 days after infection. Error bars indicate the standard deviation of three independent samples.

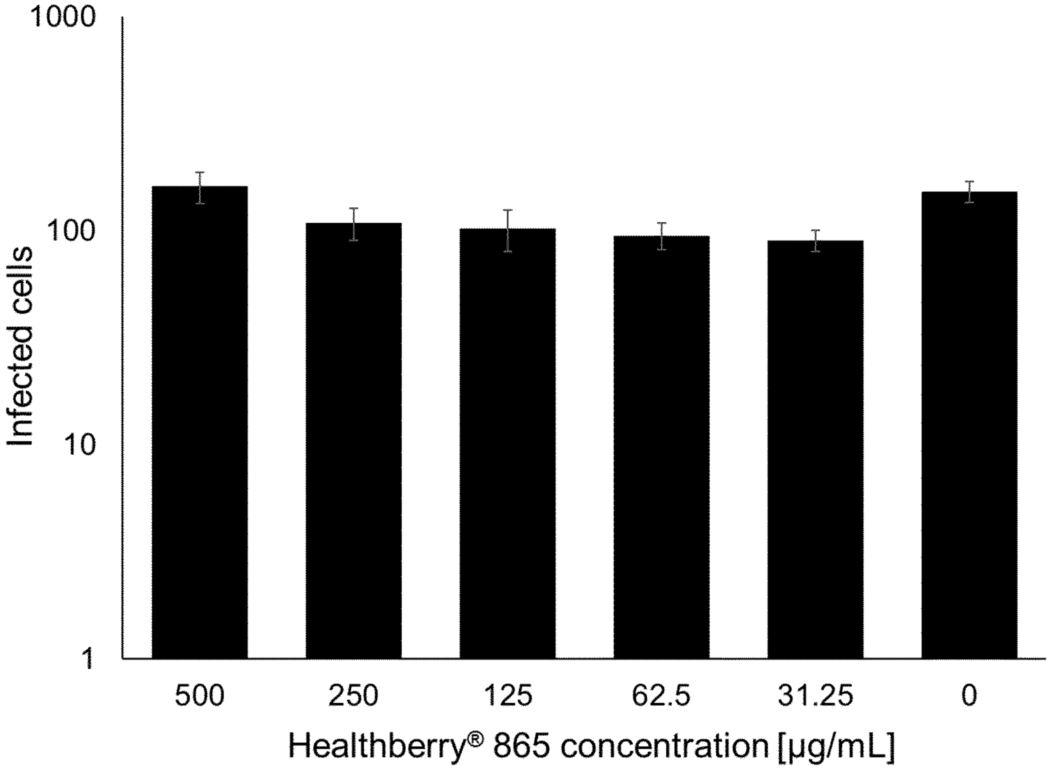
Figure 9: Healthberry® 865 does not inhibit the CD46 mediated infection of the Edmonston strain. Vero cells were incubated with Healthberry® 865. Bars represent the mean of six independent infections. Error bars indicated the standard deviation.

PREPARATIONS CONTAINING BERRY EXTRACTS FOR USE IN THE PROPHYLAXIS AND/OR TREATMENT OF VIRAL INFECTIONS CAUSED BY PARAMYXOVIRIDAE

CROSS-REFERENCE TO RELATED APPLICATIONS

The present application is the national stage of international application PCT/EP2020/058642, filed on Mar. 27, 2020, and claims the benefit of the filing date of European Appl. No. 19166036.4 and 19166060.4, each filed on Mar. 29, 2019.

BACKGROUND OF THE INVENTION

Field of the Invention

The present invention is related to a composition for use in treating or preventing a virus infection in a subject, wherein the virus is from the Paramyxoviridae family and wherein the composition comprises an extract of black currants and bilberries.

Description of Related Art

Anthocyanins are water-soluble vacuolar pigments that may appear red, purple or blue, depending on the surrounding pH-value. Anthocyanins belong to the class of flavonoids, which are synthesized via the phenylpropanoid pathway. They occur in all tissues of higher plants, mostly in flowers and fruits and are derived from anthocyanidins by addition of sugars. Anthocyanins are glycosides of flavylium salts. Each anthocyanin thus comprises three component parts: the hydroxylated core (the aglycone); the saccharide unit; and the counterion. Anthocyanins are naturally occurring pigments present in many flowers and fruit and individual anthocyanins are available commercially as the chloride salts, e.g. from Polyphenols Laboratories AS, Sandnes, Norway. The most frequently occurring anthocyanins in nature are the glycosides of cyanidin, delphinidin, malvidin, pelargonidin, peonidin and petunidin.

It is known that anthocyanins, especially resulting from fruit intake, have a wide range of biological activities, including antioxidant, anti-inflammatory, antimicrobial and anti-carcinogenic activities, improvement of vision, induction of apoptosis, and neuroprotective effects. Particularly suitable fruit sources for the anthocyanins are cherries, bilberries, blueberries, black currants, red currants, grapes, cranberries, strawberries, and apples and vegetables such as red cabbage. Bilberries, in particular *Vaccinium myrtillus*, and black currants, in particular *Ribes nigrum*, are especially suitable.

Bilberries contain diverse anthocyanins, including delphinidin and cyanidin glycosides and include several closely related species of the genus *Vaccinium*, including *Vaccinium myrtillus* (bilberry), *Vaccinium uliginosum* (bog bilberry, bog blueberry, bog whortleberry, bog huckleberry, northern bilberry, ground hurts), *Vaccinium caespitosum* (dwarf bilberry), *Vaccinium deliciosum* (Cascade bilberry), *Vaccinium membranaceum* (mountain bilberry, black mountain huckleberry, black huckleberry, twin-leaved huckleberry), *Vaccinium ovalifolium* (oval-leafed blueberry, oval-leaved bilberry, mountain blueberry, high-bush blueberry).

Dry bilberry fruits of *V. myrtillus* contain up to 10% of catechin-type tannins, proanthocyanidins, and anthocyanins.

The anthocyanins are mainly glucosides, galactosides, or arabinosides of delphinidin, cyanidin, and—to a lesser extent—malvidin, peonidin, and petunidin (cyanidin-3-O-glucoside (C3G), delphinidin-3-O-glucoside (D3G), malvidin-3-O-glucoside (M3G), peonidin-3-O-glucoside and petunidin-3-O-glucoside). Flavonols include quercetin- and kaempferol-glucosides. The fruits also contain other phenolic compounds (e.g., chlorogenic acid, caffeic acid, o-, m-, and p-coumaric acids, and ferulic acid), citric and malic acids, and volatile compounds.

Black currant fruits (*R. nigrum*) contain high levels of polyphenols, especially anthocyanins, phenolic acid derivatives (both hydroxybenzoic and hydroxycinnamic acids), flavonols (glycosides of myricetin, quercetin, kaempferol, and isorhamnetin), and proanthocyanidins (between 120 and 166 mg/100 g fresh berries). The main anthocyanins are delphinidin-3-O-rutinoside (D3R) and cyanidin-3-O-rutinoside (C3R), but delphinidin- and cyanidin-3-O-glucoside (D3G, C3G) are also found (Gafner, Bilberry—Laboratory Guidance Document 2015, Botanical Adulterants Program).

EP 1443948 A1 relates to a process for preparing a nutritional supplement (nutraceutical) comprising a mixture of anthocyanins from an extract of black currants and bilberries. Anthocyanins were extracted from cakes of fruit skin produced as the waste product in fruit juice pressing from *V. myrtillus* and *R. nigrum*. It could be shown that the beneficial effects of individual anthocyanins are enhanced if instead of an individual anthocyanin, a combination of different anthocyanins is administered orally, in particular a combination comprising both mono and disaccharide anthocyanins. It is thought that the synergistic effect arises at least in part from the different solubilities and different uptake profiles of the different anthocyanins.

Viruses belonging to the Paramyxoviridae virus family are associated with various diseases, such as measles (measles virus, MeV) and mumps (mumps virus, MuV). The human parainfluenza viruses (HPIV) are the second most common causes of respiratory tract disease in infants and children. There are four types of HPIVs, known as HPIV-1, HPIV-2, HPIV-3 and HPIV-4. HPIV-1 and HPIV-2 may cause cold-like symptoms, along with croup in children. HPIV-3 is associated with bronchiolitis, bronchitis, and pneumonia. HPIV-4 is known to cause mild to severe respiratory tract illnesses.

Hendra virus (HeV) and Nipah virus (NiV) in the genus Henipavirus have emerged in humans and livestock in Australia and Southeast Asia. Both viruses are contagious, highly virulent, and capable of infecting several mammalian species and causing potentially fatal disease. Due to the lack of a licensed vaccine or antiviral therapies, HeV and NiV are designated as biosafety level (BSL) 4 agents.

Measles viruses are highly contagious pathogens, which cause a temporary immunodeficiency in the infected patients leading in cases to severe complications such blindness, encephalitis), severe diarrhoea and related dehydration, ear infections, or acute respiratory infections such as pneumonia (WHO). In rare cases, measles virus can cause fatal subacute sclerosing panencephalitis (SSPE) even decades after infection. Although a potent vaccine is available, which is effective and safe, 904 measles virus infections in the first 47 weeks of 2017 have been diagnosed in Germany probably due to growing vaccination fatigue (Epidemiologisches Bulletin, 42/2017, Robert Koch Institut). Additionally, there is no specific antiviral treatment for measles infections, so that there is still the need for new specific anti-viral treatments against it. Thus, an antiviral drug, especially for SSPE and other severe case targeting viral replication, would be desirable.

It is known that viruses use different CD (cluster of differentiation) cell surface molecules as entry points. CD46, a ubiquitous regulator of complement activation, which is found on most cells of higher primates, was identified as a measles virus receptor. Further, it was recently shown that the signaling lymphocytic activation molecule (SLAM, also called CD150), a membrane glycoprotein of the immunoglobulin superfamily, mediates cell entry of several wild-type measles virus strains and that three different morbilliviruses (measles virus, canine distemper virus, and rinderpest virus) all use SLAM (human, canine, and bovine, respectively) as a port of entry (Tatsuo et al., J. Virol. Vol. 75, 5842-50, 2001). It has been shown that measles virus can down regulate expression of its two cellular receptors on the host cell surface during infection. Further, it could be demonstrated that expression of the hemagglutinin (H) protein of measles virus was sufficient for down regulation of SLAM. There is evidence that interactions between H and SLAM in the endoplasmic reticulum (ER) can promote the down regulation of SLAM but not CD46. In addition, interactions between H and SLAM at the host cell surface can also contribute to SLAM down regulation. These results indicate that those two mechanisms can lead to the down regulation of SLAM during measles virus infection (Welstead et all, J. Virol. Vol 78, 9666-74, 2004).

The family of SLAM-related receptors (SRR) is a group of surface molecules whose main function seems to be the fine-tuning of lymphocyte responses. Members of this group of receptors are CD150 (SLAM), CD244 (2B4), CD84, CD229 (Ly-9), NTB-A (Ly-108), and CD319. Disruption of SRR function is the cause for severe immune disorders such as X-linked lymphoproliferative syndrome (XLP), where XLP patients carry a mutation in SLAM-associated protein (SAP) (SH2D1A), an important adaptor molecule for the signal transduction of SRR. (Bhat et al., J. Leukoc. Biol., Vol. 79, 417-424, 2006).

The SLAM 1 protein in humans is encoded by the SLAMF1 gene and has been designated as a cell differentiating surface cluster CD150. It is found to have major roles for specific cytokine network players in a human individual, especially expressed in T, B cells in thymus. It is expressed on mature CD83+ and CD40 dendritic cells and is up-regulated by IL-1 beta. It directly mediates the production of inflammatory cytokines. Early B-cell factor 1 (EBF1) is required for the expression of SLAMF1 gene in B cells. STAT6, IRF4, and NF-kB factors involved in the transfer of the signals from the B cell receptor, its co-receptors and IL-4R, are all intertwined strongly in the regulation of SLAMF1 expression. High levels of SLAM are expressed by activated T cells, immature thymocytes, memory T cells, and a proportion of B cells and dendritic cells (Schneider et al., J. Virol. Vol 76, 7460-67, 2002). Two major immune functions have been described for CD150 in in vitro human studies, co-stimulation of T cell proliferation and augmentation of the interferon γ (IFN-γ) response (Cocks et al., Nature 378, 260-263, 1995). CD150 acts in conjunction with ion-channels, signaling via kinases and triggering energy consuming cell morphology changes (actin skeleton remodeling) as well as large particle endocytosis (Schwartz et al., Biochim. et Biophys. Acta (BBA)—Gene Regulatory Mechanisms, 1859 (10): 1259-68, 2016).

Cytokines are a category of signaling molecules that mediate and regulate immunity, inflammation, hematopoiesis, and many other cellular processes, forming a cytokine network. This network is one important physiological target where anthocyanins and their metabolites as well as hydrolyzed forms get in contact with all blood cells, B and T cells and lymphocytes (lymph, blood, lymph nodes and tissues). In this corresponding compartment, they are promoting and expressing cytokine receptors and cytokines, which are secreted. Immune cells will proliferate after activation and secrete specifically or unspecifically upon receptor and receptor-cofactor activation. Moreover, there is a need for a fine-tuned up- and down regulation to balance the immune response to prevent overshooting side effects such as shock or loss of organ function.

Those cytokines are known for their inhibited or exaggerated role in cancer (loss of immune function and programmed cell death response), immune defects or allergies (loss of moderation) and play a critical role in the clinical fate of most pathogenic virus diseases. This interconnection of the cellular cytokine network is the reason why primary clinical markers like fatigue and fever do not correlate with the survival rate of critical infections such as measles and Ebola.

It is therefore crucial during different phases of such diseases to allow specific and basal cytokine network responses and to still allow a specific co-factor selective activation for immune cell proliferation as shown in our experiments.

In this context, it is of primary clinical and nutritive interest to find safe nontoxic active food and therapeutic ingredients which interfere to stabilize the healthy phenotype (input-output and response) of the cytokine network. This is especially important before the virus signals and virus proliferation overrule the healthy cytokine network cells by its many diverse evolutionary emerged ways to interfere with the normal metabolism and anabolism.

All cellular inhibitory (acetyl ascorbic acid) or enzyme inhibiting (COX I, II) compounds including steroidal or non-steroidal anti-inflammatory effectors such as leukotriene-modifying drugs globally modify up- or downstream of inflammatory response and show toxicity such as the (e.g. gastric) damaging effects of any prostaglandin synthesis suppression. However, inflammation depends on the release of tissue factors such as histamines, leukotrienes, and prostaglandins. Steroids prevent this production of leukotrienes, via the arachidonic acid pathway, while nonsteroidal anti-inflammatory drugs more selectively prevent it either via the lipoxygenase (LO) or the cyclooxygenase (CO) pathway. In addition to their anti-inflammatory effects, those drugs also retard fibroblastic growth and proliferation which is a toxic effect.

BRIEF SUMMARY OF THE INVENTION

In the context it was surprisingly found that extracts of black currants and bilberries mediate strong inhibition of measles virus infection and replication, and the combination shows a surprising synergistic effect. Results potentially connect this function to anthocyanins and anthocyanin metabolites contained in the berry extract.

BRIEF DESCRIPTION OF THE DRAWINGS

The present invention will be described in even greater detail below based on the exemplary figures, which illustrate the following:

FIG. 1: illustrates the influence of Healthberry® 865 formulations on the viability of Vero Slam cells based on luciferase activity, measured at nine different time-points, normalized to the increase of control cells incubated with the medium, with error bars represent the standard deviation;

FIG. 2: illustrates the influence of Healthberry® 865 formulations on inhibition of measles virus infection with microscopy pictures for Healthberry® 865 concentrations of 125 and 250 μg/mL, with infected cells being visualized by fluorescence microscopy;

FIG. 3: illustrates the inhibition of viral infections by different concentrations of Healthberry® 865 formulations determined by fluorescence measurement;

FIG. 4: illustrates the inhibition of viral replication by de-stained version of Healthberry® 865 formulation based on Vero-Slam cells being infected with GFP-encoding measles virus;

FIG. 5: illustrates the effect of Healthberry® 865 formulations on measles virus infection of Vero Slam cells on logarithmic scale;

FIG. 7: illustrates the influence of Healthberry® 865 formulations on replication of influenza virus;

FIG. 8: illustrates the influence of Bilberry and Black currant extracts on measles virus infections of Vero Slam cells in contrast to Healthberry® 865 formulations on logarithmic scale; and FIG. 9: illustrates the influence of Healthberry® 865 formulations on CD46 mediated infection of the Edmonston strain.

DETAILED DESCRIPTION OF THE INVENTION

Figure 6A:
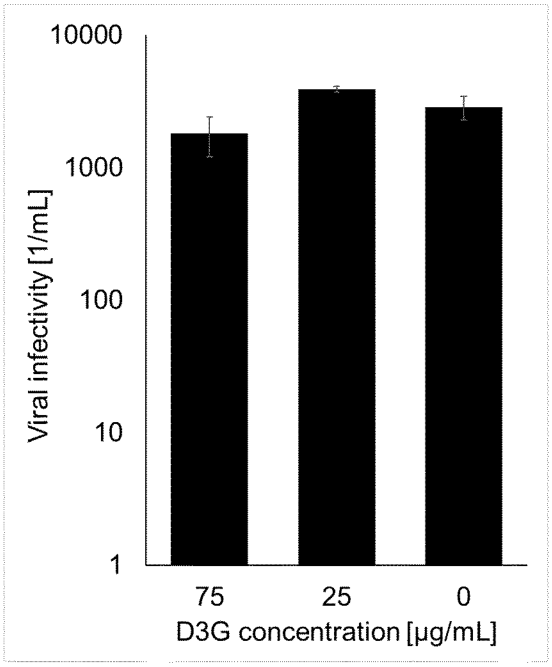
FIG. 6: illustrates the influence of D3R on viral replication on logarithmic scale using the PerkinElmer Ensight system for counting cells.

The present invention is related to a composition for use in treating or preventing a virus infection in a subject, wherein the virus is from the Paramyxoviridae family and wherein the composition comprises an extract of black currants and bilberries.

The virus family Paramyxoviridae further contains the genera Aquaparamyxovirus (fish hosts), Avulavirus (birds hosts), Ferlavirus (unknown hosts), Henipavirus (bats hosts), Morbillivirus (human, dogs, cats, cetaceans hosts), Respirovirus (rodents, human hosts), Rubulavirus (human, apes, pigs, dogs hosts).

The composition according to the present invention is especially for use in treating or preventing a virus infection in human hosts selected from

- measles virus, MeV
- mumps virus, MuV
- human parainfluenza viruses HPIV-1, HPIV-2, HPIV-3 and HPIV-4
- Hendra virus (HeV) and
- Nipah virus (NiV).

It is further also preferred to use the composition according to the present invention for treating or preventing a virus infection with canine distemper virus (CDV), cetacean morbillivirus (CeMV), feline morbillivirus (FeMV), peste-des-petits-ruminants virus (PPRV), distemper virus (PDV), rinderpest virus (RPV), bovine parainfluenza virus 3 (BPIV-3), Sendai virus (SeV), porcine parainfluenza virus 1 (PPIV-1), Achimota virus 1 (AchPV-1), Achimota virus 2 (AchPV-2), bat mumps virus (BMV), parainfluenza virus 5 (PIV-5), Hervey virus (HerV), Mapuera virus (MapV), Menangle virus (MenPV), La Piedad Michoacan Mexico virus (LPMV), simian virus 41 (SV-41), Sosuga virus, Teviot virus (TevPV), Tioman virus (TioPV), Tuhoko virus 1 (ThkPV-1), Tuhoko virus 2 (ThkPV-2), Tuhoko virus 3 (ThkPV-3).

In a preferred embodiment, the black currants are the fruit of *Ribes nigrum* and the bilberries are the fruit of *Vaccinium myrtillus*. It is further preferred, when the composition contains an extract from black currants and bilberries in a weight ratio of 0.5:1 to 1:0.5. In an advantageous configuration of the present invention, the composition is an extract of the pomaces from black currants and bilberries.

It is particularly preferred, when the composition comprises anthocyanins and the anthocyanins are present in the composition at a concentration of at least 25 weight-%, preferably at least 30 weight-%, or at least 35 weight-%, or at least 40 weight-%, or at least 45 weight-%, or at least 50 weight-%.

It is preferred, according to the present invention, when the extract is an alcoholic extract, preferably a methanol extract. The extract is preferably produced by a process comprising the steps of

- extraction of black currants and bilberries,
- purification via chromatography,
- mixing of the extract(s) with water and
- spray-drying of the mixture.

One example of such a process is disclosed in EP1443948. In a preferred embodiment, maltodextrin is added to the composition.

A further preferred embodiment is directed to a composition for use in treating or preventing a virus infection in a subject, wherein the virus is from the Paramyxoviridae family and wherein the composition comprises delphinidin 3-rutinoside (D3R) according to the following formula:

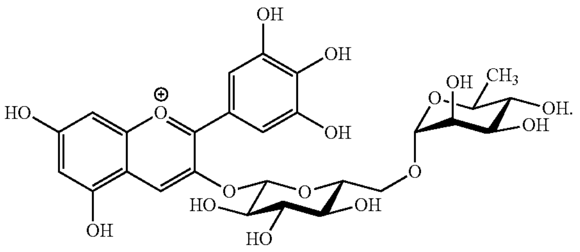

It is also intended to include pharmaceutically acceptable polymorphs, prodrugs, isomers, salts and derivatives of D3R.

D3R, also known as tulipanin is an anthocyanin found in black currants and other fruits and flowers can be used from a natural origin or can be synthesized in vitro or in vivo. D3R can be found in Peruvian lily (*Alstroemeria* spp.), berberis (*Berberis* spp.), princess vine (*Cissus sicyoides*), Hymenocallis (*Hymenocallis* spp.), Cassava (*Manihot utilissima*), *Musa acuminata*, dwarf lilyturf (*Ophiopogon japonicus*), *Petunia exserta, Petunia reitzii*, black currant (*Ribes nigrum*), Rye (*Secale cereal*), tamarillo (*Solanum betaceum*), *Thaumatococcus danieffii, Tulipa* spp. and in eggplants. It is preferred to use extracts of fruits, preferably of black currants as a source of D3R.

The composition according to the present invention preferably contains at least three monosaccharide anthocyanins. Moreover, it preferably contains at least one monosaccharide anthocyanin in which the saccharide is arabinose or at least one disaccharide anthocyanin in which the disaccharide is rutinose. The composition preferably contains anthocyanins with at least two different aglycones, more preferably at least four. Especially preferably the composition contains anthocyanins in which the aglycone units are cyanidin, peonidin, delphinidin, petunidin, malvidin and optionally also pelargonidin. In one preferred embodiment, the composition also contains at least one trisaccharide anthocyanin. The disaccharide anthocyanins are more water-soluble than the monosaccharides; moreover, cyanidin and delphinidin anthocyanins are amongst the most water-soluble anthocyanins.

In an advantageous embodiment of the present invention anthocyanins are selected from cyanidin-3-glucoside, cyanidin-3-galactoside, cyanidin-3-arabinoside, delphinidin-3-glucoside, delphinidin-3-galactoside, delphinidin-3-arabinoside, petunidin-3-glucoside, petunidin-3-galactoside, petunidin-3-arabinose, peonidin-3-glucoside, peonidin-3-galactoside, peonidin-3-arabinose, malvidin-3-glucoside, malvidin-3-galactoside, malvidin-3-arabinose, cyanidin-3-rutinoside, delphinidin-3-rutinoside. The anthocyanins are preferably selected from cyanidin-3-glucoside, cyanidin-3-rutinoside, delphinidin-3-glucoside, delphinidin-3-rutinoside, cyanidin-3-galactoside, delphinidin-3-galactoside.

The anthocyanins can be from natural sources or from synthetic productions. Natural sources are preferably selected from fruits, flowers, leaves, stems and roots, preferably violet petal, seed coat of black soybean. Preferably anthocyanins are extracted from fruits selected from: ąćaí, black currant, aronia, eggplant, blood orange, marion blackberry, black raspberry, raspberry, wild blueberry, cherry, queen Garnet plum, red currant, purple corn (*Z. mays* L.), concord grape, norton grape, muscadine grape, red cabbage, okinawan sweet potato, Ube, black rice, red onion, black carrot. Particularly suitable fruit sources for the anthocyanins are cherries, bilberries, blueberries, black currants, red currants, grapes, cranberries, strawberries, black chokeberry, and apples and vegetables such as red cabbage. Bilberries, in particular *Vaccinium myrtillus*, and black currants, in particular *Ribes nigrum*, are especially suitable. It is further preferred to use plants enriched with one or more of anthocyanins as natural sources, preferably plants enriched with delphinidin-3-rutinoside.

The counterion in the anthocyanins in the composition of the invention may be any physiologically tolerable counter anions, e.g. chloride, succinate, fumarate, malate, maleate, citrate, ascorbate, aspartate, glutamate, etc. Preferably however the counterion is a fruit acid anion, in particular citrate, as this results in the products having a particularly pleasant taste. Besides the anthocyanins, the composition may desirably contain further beneficial or inactive ingredients, such as vitamins (preferably vitamin C), flavones, isoflavones, anticoagulants (e.g. maltodextrin, silica, etc.), desiccants, etc.

In a preferred embodiment, the virus is from the genus Morbillivirus, Respirovirus or Rubulavirus, preferably measles virus. In a further preferred embodiment, the composition inhibits or prevents entry of the virus into a host cell or inhibits replication of the virus.

It is preferred when the composition comprises anthocyanins and is to be administered to the subject in a dose of the anthocyanins/regimen of 1 to 10 oral dosages of at least 80 mg anthocyanins each per day, preferably 3 to 6 oral dosages of at least 80 mg anthocyanins each per day.

In a further advantageous configuration, the composition is to be administered to the subject as parenteral bolus injection or infusion or parenteral nutritional solution. It is also preferred to use the composition to stabilize critical patients, where lifesaving treatments are not effective, and no last-line treatment is available (due to lack of treatment options).

The composition according to the present invention is to be administered to the subject, reaching a concentration in the target compartment at least 30 μg/ml, preferably at least 100 μg/ml. Target compartment are blood and lymph, specifically the medium surrounding the cells of the immune system infected by the Paramyxoviridae, preferably Peripheral Blood Mononuclear Cells (PBMCs).

In a preferred embodiment, the subject is a human and has preferably not received a measles vaccination or has not previously been exposed to the measles virus, or the subject is pregnant, or younger than 15 months.

The current invention is also directed to a liquid composition comprising an extract of black currants and bilberries, wherein the composition is comprised in a nebulizer. In an alternative configuration the liquid composition comprises delphinidin-3-rutinoside as active ingredient.

The invention also refers to a nasal spray or throat spray liquid composition comprising an extract of black currants and bilberries, wherein the composition further comprises a pharmaceutically acceptable excipient suitable for a liquid composition that is to be administered to the mucosal surfaces of the nose, mouth and throat, preferably wherein the excipient comprises one or more of a tonicity adjusting agent, a buffering agent, a preservative, an antioxidant, a stabilizer, a pH adjusting agent, a penetration enhancer, a surfactant and a humectant.

The invention also provides a composition formulated as a nasal spray, nasal drops, a nasal powder, a nasal wash, a nasal stick, a throat spray, a throat lozenge or a mouthwash, and that these compositions will further comprise a pharmaceutically acceptable carrier suitable for a composition that is to be administered to the mucosal surfaces of the nose, mouth and throat.

A further aspect of the present invention is referring to a baby milk formula as in the form of a stabilized dispersion or microemulsion, wherein the baby milk formula comprises an extract of black currants and bilberries, and preferably wherein the formula provides a mixture of at least one protein, at least one fat, at least one carbohydrate, vitamins and minerals suitable as nutrients for a baby of less than 12 months.

A further aspect of the present invention is related to a sterile i.v. composition/premix with excipients for parenteral nutrition, such as albumin, human protein fraction, blood fractions, salts, electrolytes, carbohydrates etc.

The present invention is also related to a sterile aqueous composition suitable for intravenous administration, the sterile composition comprising an extract of black currants and bilberries, preferably wherein the sterile composition is isotonic and/or comprises saline solution, more preferably wherein the sterile composition further comprises one or more of carbohydrates, proteins, amino acids, lipids, salts, and multivitamins.

The present invention also refers to a composition comprising an analgesic or topical anaesthetic and an extract of black currants and bilberries, preferably wherein the analgesic is ibuprofen or paracetamol/acetaminophen, a composition for use in treating pain associated with measles in a subject, a combined preparation comprising an analgesic or topical anaesthetic, and an extract of black currants and bilberries, for simultaneous, separate or sequential use in medicine,

- a throat lozenge comprising an analgesic a topical anaesthetic, and an extract of black currants and bilberries, preferably wherein the topical anaesthetic is benzocaine, or menthol,
- a composition comprising an antipyretic, and an extract of black currants and bilberries,
- a composition for use in treating fever associated with measles in a subject,
- a combined preparation comprising an antipyretic, and an extract of black currants and bilberries, for simultaneous, separate or sequential use in medicine,
- a composition comprising a decongestant, and an extract of black currants and bilberries,
- a composition in the form of a nasal spray,
- a combined preparation comprising a decongestant, and an extract of black currants and bilberries, for simultaneous, separate or sequential use in medicine,
- a composition comprising vitamin A and an extract of black currants and bilberries,
- a composition according to the previous claim for use in preventing measles in a subject,
- a combined preparation comprising vitamin A and an extract of black currants and bilberries for simultaneous, separate or sequential use in medicine.

A combined preparation is one which comprises separately packaged active components which are to be combined in use, i.e. by being administered simultaneously, separately or sequentially to the subject.

Analgesic compounds are preferably selected from acetylsalicylic acid, Diclofenac, Dexibuprofen, Dexketoprofen, Flurbiprofen, Ibuprofen, Indometacin, Ketoprofen, Meloxicam, Nabumeton, Naproxen, Phenylbutazon, Piroxicam, Phenazon, Propyphenazon, rofecoxib, Celecoxib, Etoricoxib, Parecoxib, Metamizol, Paracetamol/Acetaminophen.

For all the compositions described above it is advantageous, when the black currants are the fruit of *Ribes nigrum* and/or the bilberries are the fruit of *Vaccinium myrtillus*. It is further preferred, when the composition contains an extract from black currants and bilberries in a weight ratio of 0.5:1 to 1:0.5. In an advantageous configuration of the present invention, the composition is an extract of the pomaces from black currants and bilberries. It is particularly preferred, when the composition comprises anthocyanins and the anthocyanins are present in the composition at a concentration of at least 25 weight-%, preferably at least 30 weight-%, or at least 35 weight-%, or at least 40 weight-%, or at least 45 weight-%, or at least 50 weight-%. It is preferred, according to the present invention, when the extract is an alcoholic extract, preferably a methanol extract.

The present invention is also related to an antiviral agent for treating or preventing a virus infection in a subject, wherein the virus is from the Paramyxoviridae family with a level of efficacy of 2 log levels, and an antiviral agent which is non-toxic.

The present invention is also related to an antiviral agent for treating or preventing a virus infection in a subject, wherein the virus is from the Paramyxoviridae family with an IC50 value (in vitro evaluation) of 60 μg/mL.

The invention is also referring to an antiviral agent for treating or preventing a virus infection in a subject, wherein the virus is from the Paramyxoviridae family with a level of efficacy of 2 log levels, which is not killing more than 30%, preferably not more than 20%, more preferably not more than 10% of cells in a cell-based assay in mammalian cells, preferably Vero cells.

This antiviral agent preferably comprises one or more anthocyanins selected from cyanidin-3-glucoside, cyanidin-3-galactoside, cyanidin-3-arabinoside, delphinidin-3-glucoside, delphinidin-3-galactoside, delphinidin-3-arabinoside, petunidin-3-glucoside, petunidin-3-galactoside, petunidin-3-arabinose, peonidin-3-glucoside, peonidin-3-galactoside, peonidin-3-arabinose, malvidin-3-glucoside, malvidin-3-galactoside, malvidin-3-arabinose, cyanidin-3-rutinoside, delphinidin-3-rutinoside. The anthocyanins are preferably selected from cyanidin-3-glucoside, cyanidin-3-rutinoside, delphinidin-3-glucoside, delphinidin-3-rutinoside, cyanidin-3-galactoside, delphinidin-3-galactoside.

Moreover, it was found that extracts of black currants and bilberries mediate strong inhibition of measles virus infection and replication and specifically inhibit CD150 function. Results potentially connect this function to anthocyanins and anthocyanin metabolites contained in the berry extract and to the modulation of immune response.

The present invention is also related to a composition for use in inhibiting CD150 function in a subject wherein the composition comprises an extract of black currants and bilberries.

Preferably, the composition is for treating or preventing an immune system disorder or an infectious disease in a subject by inhibiting CD150 function. The composition preferably acts on energy consuming cell morphology changes to stabilize the selective co-factor activation capabilities and nurturing the healthy T and B cell status.

Item List

Preferred embodiments of the present invention are summarized in the following item list:

1. A composition for use in treating or preventing a virus infection in a subject, wherein the virus is from the Paramyxoviridae family and wherein the composition comprises an extract of black currants and bilberries.
2. The composition for use according to item 1, wherein the black currants are the fruit of *Ribes nigrum* and/or the bilberries are the fruit of *Vaccinium myrtillus*.
3. The composition for use according to any preceding item wherein the composition contains an extract from black currants and bilberries in a weight ratio of 0.5:1 to 1:0.5.
4. The composition for use according to any preceding item wherein the composition is an extract of the pomaces from black currants and bilberries.
5. The composition for use according to any preceding item, wherein the composition comprises anthocyanins and the anthocyanins are present in the composition at a concentration of at least 25 weight-%.
6. The composition for use according to any preceding item, wherein the extract is an alcoholic extract, preferably a methanol extract.
7. The composition for use according to any preceding item, wherein the extract is prepared by a process comprising the steps of extraction of black currants and/or bilberries, purification via chromatography, mixing of the extract(s) with water and spray-drying of the mixture.
8. A composition for use in treating or preventing a virus infection in a subject, wherein the virus is from the Paramyxoviridae family and wherein the composition comprises delphinidin-3-rutinoside having the following formula:

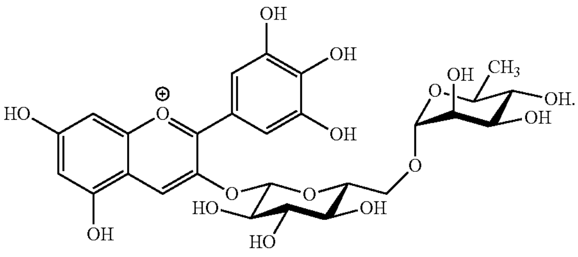

9. A composition for use according to item 8, further comprising one or more of the following anthocyanins: cyanidin-3-glucoside, cyanidin-3-galactoside, cyanidin-3-arabinoside, delphinidin-3-glucoside, delphinidin-3-galactoside, delphinidin-3-arabinoside, petunidin-3-glucoside, petunidin-3-galactoside, petunidin-3-arabinose, peonidin-3-glucoside, peonidin-3-galactoside, peonidin-3-arabinose, malvidin-3-glucoside, malvidin-3-galactoside, malvidin-3-arabinose, cyanidin-3-rutinoside, delphinidin-3-rutinoside.
10. A composition for use according to item 8, further comprising one or more of the following anthocyanins: cyanidin-3-glucoside, cyanidin-3-rutinoside, delphinidin-3-glucoside, cyanidin-3-galactoside, delphinidin-3-galactoside, preferably comprising all anthocyanins listed.
11. The composition for use according to any preceding item wherein the virus is from the genus Morbillivirus, Respirovirus or Rubulavirus.
12. The composition for use according to any preceding item wherein the virus is measles virus.
13. The composition for use according to any preceding item wherein the composition inhibits or prevents entry of the virus into a host cell.
14. The composition for use according to any preceding item wherein the composition inhibits replication of the virus.
15. The composition for use according to any preceding item wherein the composition comprises anthocyanins and is to be administered to the subject 1 to 10 oral dosages of at least 80 mg anthocyanins each per day, preferably 3 to 6 oral dosages of at least 80 mg anthocyanins each per day.
16. The composition for use according to any preceding item wherein the composition is to be administered to the subject as parenteral bolus injection or infusion or parenteral nutritional solution.
17. The composition for use according to any preceding item wherein the composition is to be administered to the subject, reaching a concentration in the target compartment at least 30 μg/ml, preferably at least 100 μg/ml.
18. The composition for use according to any preceding item wherein the subject is a human.
19. The composition for use according to any preceding item wherein the subject is human and has not received a measles vaccination or has not previously been exposed to the measles virus.
20. The composition for use according to any preceding item wherein the subject is pregnant.
21. The composition for use according to any preceding item wherein the subject is human and is younger than 15 months.
22. The composition for use according to any preceding item wherein the composition is for use in inhibiting CD150 function in the subject.
23. A composition for use in inhibiting CD150 function in a subject wherein the composition comprises an extract of black currants and bilberries.
24. The composition for use according to any preceding item for treating or preventing an immune system disorder or an infectious disease in a subject by inhibiting CD150 function.
25. The composition for use according to the preceding item wherein the immune system disorder is an autoimmune disease, preferably selected from multiple sclerosis (MS), rheumatoid arthritis (RA), psoriasis, psoriatic arthritis, colitis ulcerosa, Crohn's disease, myasthenia gravis (MG), autoimmune polyglandular syndrome type II (APS-II), Hashimoto's thyroiditis (HT), type-1 diabetes (T1D), systemic lupus erythematosus (SLE), autoimmune lymphoproliferative syndrome (ALS), Parkinson's disease, or an allergy or asthma.
26. The composition for use according to any preceding item for acting on energy consuming cell morphology changes to stabilize the selective co-factor activation capabilities and nurturing the healthy T and B cell status.
27. The composition for use according to any preceding item wherein the composition inhibits or prevents entry of a Morbillivirus, preferably measles virus, into a host cell.
28. The composition for use according to any preceding item wherein antigen-specific T cell proliferation and interferon-γ production are reduced.
29. A liquid composition comprising an extract of black currants and bilberries, wherein the composition is comprised in a nebulizer.
30. A nasal spray or throat spray liquid composition comprising an extract of black currants and bilberries, wherein the composition further comprises a pharmaceutically acceptable excipient suitable for a liquid composition that is to be administered to the mucosal surfaces of the nose, mouth and throat, preferably wherein the excipient comprises one or more of a tonicity adjusting agent, a buffering agent, a preservative, an antioxidant, a stabilizer, a pH adjusting agent, a penetration enhancer, a surfactant and a humectant.
31. A baby milk formula in the form of a stabilized dispersion or microemulsion, wherein the baby milk formula comprises an extract of black currants and bilberries, and preferably wherein the formula provides a mixture of at least one protein, at least one fat, at least one carbohydrate, vitamins and minerals suitable as nutrients for a baby of less than 12 months.
32. A sterile aqueous composition suitable for intravenous administration, the sterile composition comprising an extract of black currants and bilberries, preferably wherein the sterile composition is isotonic and/or comprises saline solution, more preferably wherein the sterile composition further comprises one or more of carbohydrates, proteins, amino acids, lipids, salts, and multivitamins.
33. A composition comprising an analgesic or topical anaesthetic and an extract of black currants and bilberries, preferably wherein the analgesic is ibuprofen or paracetamol/acetaminophen.
34. A composition according to the previous item for use in treating pain associated with measles in a subject.

35. A combined preparation comprising an analgesic or topical anaesthetic or an anti-inflammatory agent and an extract of black currants and bilberries, for simultaneous, separate or sequential use in medicine.
36. A throat lozenge comprising a topical anaesthetic, and an extract of black currants and bilberries, preferably wherein the topical anaesthetic is benzocaine, or menthol.
37. A composition comprising an antipyretic, and an extract of black currants and bilberries.
38. A composition according to the previous item for use in treating fever associated with measles in a subject.
39. A combined preparation comprising an antipyretic, and an extract of black currants and bilberries, for simultaneous, separate or sequential use in medicine.
40. A composition comprising a decongestant, and an extract of black currants and bilberries.
41. A composition according to the previous item in the form of a nasal spray.
42. A combined preparation comprising a decongestant, and an extract of black currants and bilberries, for simultaneous, separate or sequential use in medicine.
43. A composition comprising vitamin A and an extract of black currants and bilberries.
44. A composition according to the previous item for use in preventing measles in a subject.
45. A combined preparation comprising vitamin A and an extract of black currants and bilberries for simultaneous, separate or sequential use in medicine.
46. A method for treating or preventing a virus infection in a subject in need thereof comprising administering to the subject an effective amount of a composition comprising an extract of black currants and bilberries, wherein the virus is from the Paramyxoviridae family.
47. A method for inhibiting CD150 function in a subject in need thereof, comprising administering to the subject an effective amount of a composition comprising an extract of black currants and bilberries, optionally wherein the method inhibits or prevents entry of a virus into a host cell.
48. A method for treating or preventing an immune system disorder or an infectious disease in a subject in need thereof by inhibiting CD150 function, the method comprising administering to the subject an effective amount of a composition comprising an extract of black currants and bilberries.
49. The method of any of items 45 to 47 wherein the composition is as defined in any of items 2 to 10.
50. The method of any of items 45 to 48, wherein the virus is as defined in item 11 or item 12.
51. The method of any of items 45 to 49, wherein the composition is to be administered according to any of items 15 to 17.

EXAMPLES

The berry extracts composition (Healthberry® 865; Evonik Nutrition & Care GmbH, Darmstadt, Germany) used in the present study is a dietary supplement consisting of 17 purified anthocyanins (all glycosides of cyanidin, peonidin, delphinidin, petunidin, and malvidin) isolated from black currant (*Ribes nigrum*) and bilberries (*Vaccinium myrtillus*).

The relative content of each anthocyanin in the Healthberry® 865 product was as follows: 33.0% of 3-O-b-rutinoside, 3-O-b-glucosides, 3-O-b-galactosides, and 3-O-b-arabinosides of cyanidin; 58.0% of 3-O-b-rutinoside, 3-O-b-glucosides, 3-O-b-galactosides, and 3-O-b-arabinosides of delphinidin; 2.5% of 3-O-b-glucosides, 3-O-b-galactosides, and 3-O-b-arabinosides of petunidin; 2.5% of 3-O-b-glucosides, 3-O-b-galactosides, and 3-O-b-arabinosides of peonidin; 3.0% of 3-O-b-glucosides, 3-O-b-galactosides, and 3-O-b-arabinosides of malvidin.

The 3-O-b-glucosides of cyanidin and delphinidin constituted at least 40-50% of the total anthocyanins.

The major anthocyanins contained in the berry extract used are cyanidin-3-glucoside, cyanidin-3-rutinoside, delphinidin-3-glucoside, delphinidin-3-rutinoside, cyanidin-3-galactoside and delphinidin-3-galactoside.

In addition to the anthocyanins mentioned above, the product also contained maltodextrin (around 40 weight-% of the composition), and citric acid (to maintain stability of anthocyanins). The amount of anthocyanin citrate is at least 25 weight-% of the composition. The composition is prepared from black currants and bilberries by a process comprising the steps of alcoholic extraction of black currants and bilberries, purification via chromatography, mixing of the extracts with maltodextrin citrate and water and spray-drying of the mixture. The product composition contains extracts of black currants and bilberries mixed in a weight ratio of around 1:1.

Materials:

TABLE 1

Materials used for the measurement of cell survival and metabolism

| Material | Supplier |
|---|---|
| RealTime-Glo ™ MT Cell Viability Assay | Promega GmbH, Mannheim (Germany) |
| Dulbecco's Modified Eagle's medium (DMEM) | Gibco Life technologies, Carlsbad (USA) |
| Fetal bovine serum | Gibco Life technologies, Carlsbad (USA) |
| Vero cells | ATCC/American Type Culture Collection in Partnership with LGC standards, Wesel (Germany) |
| Healthberry ® 865 (anthocyanin content 29.7%) | Evonik Nutrition & Care GmbH, Darmstadt (Germany) |

TABLE 2

Devices used for the measurement of cell survival and metabolism.

| Device | Supplier |
|---|---|
| Centro LB 960 microplate luminometer | Berthold Technologies, (Germany) |

TABLE 3

| Materials used for anti-viral assay | |
|---|---|
| Material | Supplier |
| GFP-encoding measles viruses | obtained from J. Schneider-Schaulies (Institute of Virology Würzburg) |
| Influenza virus serotype A | patient derived isolate (Institute of Virology Würzburg) |
| Dulbecco's Modified Eagle's medium (DMEM) | Gibco Life technologies, Carlsbad (USA) |
| Fetal bovine serum | Gibco Life technologies, Carlsbad (USA) |
| Vero Slam cells | ATCC/American Type Culture Collection in Partnership with LGC standards, Wesel (Germany) |
| MDCK cells | ATCC/American Type Culture Collection in Partnership with LGC standards, Wesel (Germany) |
| HP Viral Nucleic Acid Kit | Hoffman-La-Roche Ltd., Basel (Switzerland) |
| RTqPCR LightMix ® Modular Influenza A kit (Cat. No. 07 792 182 001) | Hoffman-La-Roche Ltd., Basel (Switzerland) |
| LightCycler ® Multiplex RNA Virus Master kit (Cat. No. 07 083 173 001) | Hoffman-La-Roche Ltd., Basel (Switzerland) |
| Healthberry ® 865 (anthocyanin content 29.7%) | Evonik Nutrition & Care GmbH, Darmstadt (Germany) |
| Bilberry extract, Vaccinium myrtillus (anthocyanin content 38.8%) | Evonik Nutrition & Care GmbH, Darmstadt (Germany) |
| Black currant extract, Ribes nigrum (anthocyanin content 30%) | Evonik Nutrition & Care GmbH, Darmstadt (Germany) |
| Berry extract analogue to Healthberry ® 865 without maltodextrin | Evonik Nutrition & Care GmbH, Darmstadt (Germany) |
| GLUCIDEX IT 19 (maltodextrin) | ROQUETTE GmbH, Frankfurt (Germany) |
| Delphinidin 3-rutinoside/D3R | Polyphenols AS, Sandnes (Norway) |
| Delphinidin 3-glucoside/D3G | Polyphenols AS, Sandnes (Norway) |
| Cyanidin 3-rutinoside/C3R | Polyphenols AS, Sandnes (Norway) |
| Cyanidin 3-glucoside/C3G | Polyphenols AS, Sandnes (Norway) |

TABLE 4

| Devices used for the anti-viral assay | |
|---|---|
| Device | Supplier |
| LightCycler96 qPCR 20 machine | Hoffman-La-Roche Ltd., Basel (Switzerland) |
| Lighcylcler96 Application software V1.1 | Hoffman-La-Roche Ltd., Basel (Switzerland) |
| TECAN saphire2 plate reader | Tecan Group AG, Männedorf (Switzerland) |
| PerkinElmer Ensight system | Perkin Elmer, Rodgau (Germany) |
| Leica fluorescence microscope | Leica Microsystems, Wetzlar (Germany) |

TABLE 5

| Materials used for CD150 (SLAM) receptor assay | |
|---|---|
| Material | Supplier |
| GFP-encoding measles viruses | obtained from J. Schneider-Schaulies (Virology Würzburg) |
| GFP-encoding measles vaccination viruses/Edmonston vaccination strain | obtained from J. Schneider-Schaulies (Virology Würzburg) |
| Dulbecco's Modified Eagle's medium (DMEM) | Gibco Life technologies, Carlsbad (USA) |
| Fetal bovine serum | Gibco Life technologies, Carlsbad (USA) |
| Vero cells | ATCC/American Type Culture Collection in Partnership with LGC standards, Wesel (Germany) |
| Healthberry ® 865 | Evonik Nutrition & Care GmbH, Darmstadt (Germany) |

TABLE 6

| Devices used for CD150 (SLAM) receptor assay | |
|---|---|
| Device | Supplier |
| PerkinElmer Ensight system | Perkin Elmer, Rodgau (Germany) |

Methods:

Test Compound Preparation:

All test compounds were dissolved and diluted in cell culture medium. The overall amount of anthocyanins was normalized between Healthberry® 865 and the single anthocyanins (e.g. 500 μg/mL of Healthberry® 865 includes the 150 μg/mL of anthocyanins tested for the single test compounds) or as well the single berry extracts (taken into account that Healthberry® 865 also contains maltodextrin besides the anthocyanins). Additionally, a "de-stained" (pretreated) version of the Healthberry® 865 solution was also tested. For the de-stained version, the Healthberry® 865 solution was incubated for 24 h at 37° C. to allow the anthocyanins to partially degrade into their metabolites.

The medium served as control for viral inhibition or cytotoxicity.

Cell Viability Assay:

Cell viability was measured by RealTime-Glo™ MT Cell Viability Assay (Cat. No. G9712, Promega, Germany). Vero-Slam cells ($2\times10^4$) were incubated with decreasing amounts of the compound solubilized in DMEM. Wells with DMEM alone served as control. The MT Cell Viability Substrate and the NanoLuc® luciferase were added according to the manufacturer's instructions. The assays were performed in triplicates. After 1 h, and then every six or 12 h, the luminescence was measured with Centro LB 960 microplate luminometer (Berthold Technologies, Germany). Luminescence values after 1 h were set to 1 and changes over time were calculated.

Anti-Viral Assay:

Measles Virus Replication:

Vero-Slam cells were incubated with decreasing concentration of the solubilized test compounds. All concentrations were analyzed on three independent six-well plates or by independent six replicates on a black 96well plate (PerkinElmer). Cells were infected with GFP-encoding wild-type measles virus and incubated for two days. Part I: Due to the autofluorescence of the compound, the medium was replaced by DMEM and GFP expressing cells were subsequently quantified by using a TECAN saphire2 plate reader (the fluorescence was measured through the bottom of the plate). Every well was measured five times at 25 spots (six-well plates) or nine places (96-well plates) utilizing the beam settings "fine" and "sensitive". Autofluorescence of a plate with untreated and non-infected cells was measured, and the mean background fluorescence intensity was subtracted from the values obtained above. Part II: Two days after infection measles virus-infected cells and GFP expressing cells were directly counted using the PerkinElmer Ensight system with optical cell culture plates. The instrument was controlled by manual counting. Viral titers were calculated as infectious particles per mL.

From the first identification till now, antiviral compounds are initially identified via screening assay either in vitro or in cell culture using replication assays. Even the activities of compounds identified by in vitro enzyme screening tests need to be verified in cell culture-based assays. These assays are state of the art methods to identify and confirm antiviral activities since they allow the quantification of the inhibition of viral replication and ensure the cellular uptake of compounds. For example, aciclovir, the gold standard in the treatment of HSV-1, was identified by screening of antiviral substances in sponges (Elion et al., 1977 Selectivity of action of an antiherpetic agent, 9-(2-hydroxyethoxymethyl) guanine. PNAS 74. 5716). Later, the antiviral activity of aciclovir inhibiting other members of the Herpesviridae was shown in cell culture-based assays as well (AKESSON-JOHANSSON et al., 1990 Inhibition of Human Herpesvirus 6 Replicationby9-[4-Hydroxy-2-(Hydroxymethyl)Butyl] Guanine (2HM-HBG) and Other Antiviral Compounds. AAC 34. 2417). Moreover, all compounds used as clinical drugs against HIV-1, such as 3TC and Lopinavir (ABT-378), were initially tested in vitro to demonstrate their antiviral effects (Coates et al., 1992. The Separated Enantiomers of 2'-Deoxy-3'-Thiacytidine (BCH 189) Both Inhibit Human Immunodeficiency Virus Replication In Vitro. AAC 36. 202; Sham et al. 1998. ABT-378, a Highly Potent Inhibitor of the Human Immunodeficiency Virus Protease. AAC 42. 3218).

Influenza Genome Determination:

MDCK cells were seeded in 48 well plates. After 24 h test compounds were added, and cells were subsequently infected with influenza A virus. All infections were performed in triplicates. Cell culture supernatants were harvested three days post-infection and centrifuged at 2000 rpm to remove detached cells and analyze viruses secreted to the supernatant. Viral RNAs were isolated from 200 µl cell culture supernatants using the Roche HP Viral Nucleic Acid Kit according to the manufacturer's manual. Viral genome copy numbers were determined using 5 µl of the eluted RNA and the RTqPCR LightMix® Modular Influenza A kit (Cat. No. 07 792 182 001, Roche) in combination with the LightCycler® Multiplex RNA Virus Master kit (Cat. No. 07 083 173 001, Roche). All PCR reactions were performed in triplicates from RNAs with a Roche LightCycler96 qPCR 20. The Cq values were determined with the respective cycler software (Roche Lighcylcler96 Application software V1.1). The internal standard of the Modular Influenza A kit with 1000 genome copies served as positive control. Quality was ensured by following the MIQE guidelines.

CD150 (SLAM) Receptor Binding Assay:

Measles viruses require SLAM (CD150) as the cellular entry receptor. The viral hemagglutinin protein (H) binds with its head domain to a beta-sheet of the membrane distal ectodomain of the CD150 receptor (Hashiguchi et al., (2011) Nature Struct. & Mol. Biol. 18, 134-141). In contrast, the measles vaccination strain Edmonston can use CD46 as cellular receptor. This fundamental difference provides an opportunity to analyze, whether the inhibition of measles virus by berry extracts is due to a specific block of viral entry. The entry of the vaccination strain should not be affected if berry extracts target viral entry in a SLAM specific way.

To test measles virus replication, Vero-Slam cells were incubated with decreasing concentration of the solubilized test compound for approx. 1 h. All concentrations were analyzed on three independent six-well plates or by independent six replicates on a black 96well plate (PerkinElmer). Cells were infected with GFP-encoding wild-type measles virus or with a recombinant GFP-encoding Edmondson strain and incubated for two days. Two days after infection measles virus-infected infected cells and GFP-expressing cells were directly counted using the PerkinElmer Ensight system with optical cell culture plates.

EXAMPLE 1

Influence of Berry Extracts on Cell Viability

To exclude cellular toxicity and adverse side effects, cellular viabilities of the test compounds on Vero-Slam cells (96 well-plate: 650 cells/well) were determined with the RealTime-Glo™ MT Cell Viability Assay kit. This assay measures the intracellular ATP content and therefore provides information on the cellular viability and metabolism. The cells were incubated with decreasing compound concentration in triplicate assays. Subsequently, both the MT Cell Viability Substrate and NanoLuc® Enzyme were added, and the luciferase activities were measured after 1 h. These measurements were repeated every 6 h or 12 h, and changes to the luciferase activity at the beginning of the experiment were calculated per individual well. The luminescence was normalized on the mean of the medium control wells for each time-point. These compensations result in values of 1 for the medium control at each time point. Values less than 1 indicate a lower number of cells or a decrease in metabolic activity compared to the appropriate controls.

FIG. 1 displays the influence of Healthberry® 865 on the viability of Vero Slam cells. The increase of luciferase activity, measured at nine different time-points, was normalized to the increase of control cells incubated with the medium. Error bars represent the standard deviation.

Healthberry® 865 did not negatively influence cellular growth or metabolic activity at any concentration analysed, indicating the compound was non-toxic at these concentrations. Healthberry® 865 even led to increased metabolic activity and viability of the cells when incubated with increasing concentrations of the extract.

EXAMPLE 2

Anti-Viral Effects of Healthberry® 865 on Measles Virus

Experimental Part 1:

Vero-Slam cells (96-well plate: 1000 cells/well) were infected with GFP encoding measles virus in the presence of either 250 μg/ml or 125 μg/ml of the test compound. The virus-containing medium was removed after 1.5 h and replaced by fresh medium containing the same concentration of the compound. This scenario mimics a treatment during virus exposure. Fluorescence was analyzed two days after infection using a Leica fluorescence microscope. More than 20 pictures per concentration were taken at the random position. The fluorescence and the bright field images were merged with the Leica software. Healthberry® 865 efficiently inhibited viral replication at 250 μg/ml. Furthermore, it blocked cell-to-cell spread and syncytia formation completely. The lower concentration of 125 μg/ml still showed some inhibition of infection. However, it prevented the formation of large syncytia typical for measles virus infection. The inhibition of cell-to-cell infection might be the key to efficiently block virus spread in infected patients since the measles virus is known to be strongly cell associated. Furthermore, the reduction of infected cells indicates that Healthberry® 865 targets replication steps prior genome replication, such as receptor recognition/binding, entry, uncoating or viral transcription.

FIG. 2: shows that Healthberry® 865 inhibits measles virus infection with microscopy pictures for Healthberry® 865 concentrations of 125 and 250 μg/mL. Vero-Slam cells were infected with GFP-encoding measles virus in the presence of the compound. Infected cells were visualized by fluorescence microscopy.

To quantify the inhibition of measles virus by Healthberry® 865, the GFP-fluorescence was measured. Vero-Slam cells (1000000 cells/well) were infected in the presence of Healthberry® 865 and incubated for 1.5 h. Then the medium was replaced, and the cells were further incubated for two days. First, non-infected and non-treated cells were measured to compensate for auto-fluorescence of the cells. The statistical mean of these measurements was subtracted from the fluorescence values. Healthberry® 865 concentrations of 63 μg/mL concentrations efficiently inhibited measles virus replication to 50%. Thus, based on the in vitro evaluation the IC50 of the test compound is expected to be in the range of 60 μg/mL.

FIG. 3 displays the inhibition of viral infections by different concentrations of Healthberry® 865 determined by fluorescence measurement. Vero-Slam cells were infected with GFP-encoding measles virus. Fluorescence was measured, each bar represents the mean of 3 independent infections and the error bars the standard deviation.

A similar experiment was performed to analyze the influence of the de-stained version on measles virus replication. Vero-Slam cells were incubated with the de-stained Healthberry® 865 at decreasing concentrations and subsequently infected with GFP-encoding recombinant measles virus. All assays were performed in triplicates. The fluorescence was measured two days after infection without the medium due to the autofluorescence of the compound. Although the de-stained version significantly inhibited the measles virus replication, the suppression was not as efficient as the fresh Healthberry® 865 solution and required higher concentrations. These results indicate active ingredients among the anthocyanins, which are continuously degraded and metabolized over the time within the de-stained and pre-incubated sample.

FIG. 4 displays the inhibition of viral replication by de-stained version of Healthberry® 865. Vero-Slam cells were infected with GFP-encoding measles virus. Fluorescence was measured, and each value represents the mean of three independent infections. Error bars represent the standard deviation.

Experimental Part 2:

To confirm our previous results and to analyze components of Healthberry® 865 separately, infection experiments with the test compounds Delphinidin 3-rutinoside (D3R), Delphinidin 3-glucoside (D3G), Cyanidin 3-rutinoside (C3R), Cyanidin 3-glucoside (C3G) and Healthberry® 865 were performed, as described before, with the GFP encoding measles virus in triplicates (Healthberry® 865) or quadruplets (all other components).

However, in contrast to the previous experiments, infected cells were counted with the PerkinElmer Ensight system, since this system allows to quantify changes in viral titers on single cell level. Berry extracts of black currants and bilberries, especially Healthberry® 865 reduced viral infection significantly even in concentrations as low as 63 μg/mL. In the concentration of 250 μg/mL a reduction of almost 2 log levels could be achieved, reaching a level similar to an anti-viral agent.

FIG. 5 shows that Healthberry® 865 reduces measles virus infection of Vero Slam cells significantly (log scale). Vero cells were infected with GFP-encoding measles virus in triplicates and GFP expressing cells were counted using the Ensight system. Error bars indicate the standard deviation of three independent samples.

Similar experiments were performed to determine the effect of D3R, D3G, C3R, C3G as well as a mixture of the four components (concentrations of the mixture equivalent to the concentration of each single component). However, only non-toxic compound concentrations were applied.

Figure 6B:
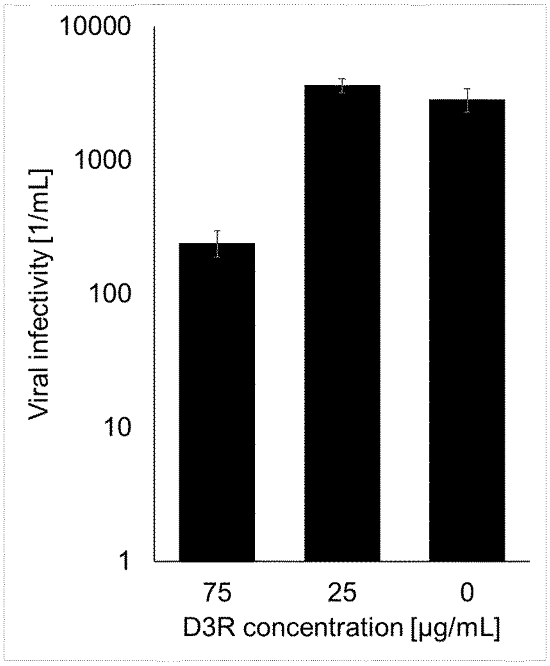
Figure 6C:
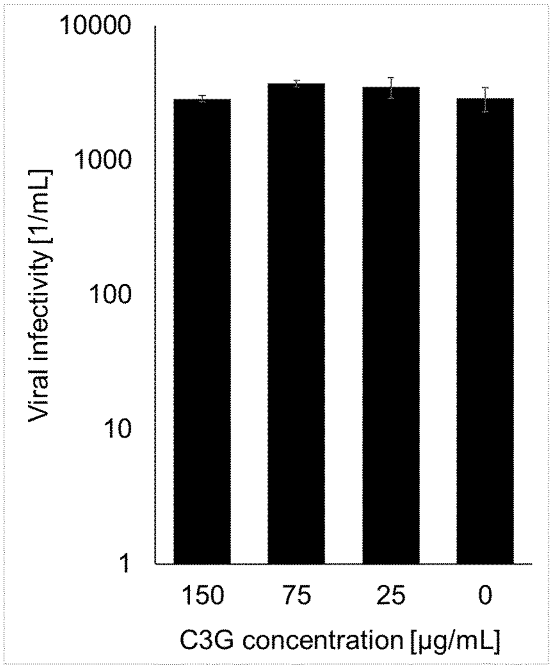
Figure 6D:
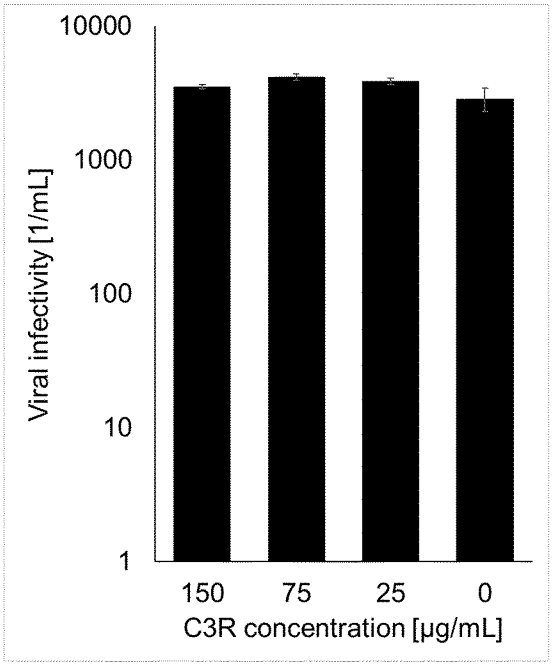
Figure 6E:
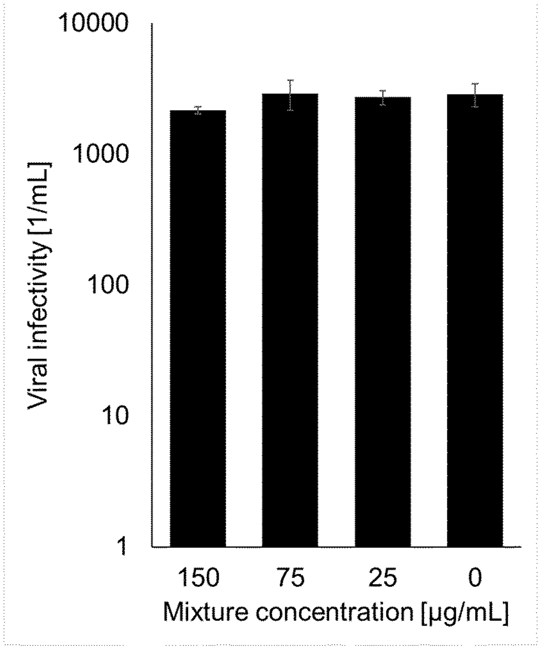

FIG. 6 displays the influences of D3R on viral replication (log scale). Cells were infected with GFP-encoding measles virus in quadruplets. Infected cells were counted with the PerkinElmer Ensight system. Error bars indicate the standard deviation of four independent samples.

The compound D3R reduced the number of infected cells at a concentration of 75 μg/mL, while the other anthocyanins as well as even the mixture of them did not influence viral replication. These results substantiate the improved properties of berry extracts of black currants and bilberries, such as Healthberry® 865 in comparison to single anthocyanins as well as pure anthocyanin mixtures.

EXAMPLE 3

Anti-Viral Effects of Healthberry® 865 on Influenza A Virus (Comparative)

The influence of Healthberry® 865 and single anthocyanins on the replication of Influenza A virus were analyzed. MDCK cells were incubated with the test compounds and subsequently infected with a patient-derived isolate of Influenza virus serotype A. All reactions were performed in triplicates. Cell culture supernatants were harvested after three days, and viral genomic RNAs were isolated from 200 μl cell culture supernatants. Viral loads were determined by RTqPCR using the LightMix® Modular Influenza A kit (Roche). Positive controls with 1000 Influenza genome copies were included in the RTqPCR. All RTqPCR reactions were performed in triplicates.

All test materials, including Healthberry® 865, showed similar amounts of virus in the supernatant as the negative control, with only minor differences indicating that none of the components inhibited influenza virus replication.

FIG. 7 shows that the replication of influenza virus is not influenced by Healthberry® 865. MDCK cells were pretreated with Healthberry® 865, infected with influenza virus (serotype A). Viral RNAs were isolated and quantified by RTqPCR (Cq-values; note: lower Cq values correspond to higher viral loads).

The results displayed no effect of Healthberry® 865 on Influenza A virus confirming the specificity of the anti-viral effects of berry extracts of black currants and bilberries on specific viruses or virus families, respectively. Other test compounds as the single anthocyanins also did not show any influence on the replication of influenza virus.

EXAMPLE 4

Anti-Viral Effects of Berry Extracts on Measles Virus

Since Healthberry® 865 is a composition of bilberry and black currant extracts, it was analyzed, whether both extracts contain the compound active against measles virus. Vero cells were incubated with 500, 250, and 125 mg/mL of Healthberry® 865, bilberry or black currant extract followed by infection with measles virus. The cells were subsequently infected with GFP-encoding measles virus, and GFP expressing cells were quantified with the Perkin Elmer Ensight reader. All infections were performed in triplicate assays.

FIG. 8 shows that neither Bilberry nor Black currant extract reduces measles virus infections of Vero Slam cells in contrast to Healthberry® 865 (log scale). Vero cells were infected with GFP-encoding measles virus in triplicates and GFP expressing cells were counted using the Ensight system. Error bars indicate the standard deviation of three independent samples.

While treatment with Healthberry® 865 resulted in a suppression of viral infectivity by one order of magnitude, both bilberry and black currant extract did not decrease the viral infectivity significantly. Thus, the generated data provide evidence that Healthberry® 865 shows a strong and unexpected synergistic effect on measles virus replication compared to the single extracts from bilberry or black currant.

EXAMPLE 5

Influence of Berry Extracts on CD150 (SLAM) Receptor-Mediated Measles Virus Infection In this experiment, Vero cells were infected with a recombinant GFP-expressing Edmonston strain in the presence of Health berry® 865.

FIG. 9 shows that Healthberry® 865 does not inhibit the CD46 mediated infection of the Edmonston strain. Vero cells were incubated with Healthberry® 865. Bars represent the mean of six independent infections and error bars indicate the standard deviation.

Healthberry® 865 did not inhibit infection by the Edmonston strain, while Healthberry® 865 suppressed viral infection of the measles wild-type strain about one order of magnitude. These results show that berry extracts block specifically the CD150 (SLAM) mediated entry of the wild-type virus and indicate an inhibition of the CD150 (SLAM) receptor function by berry extracts.

The invention claimed is:

1. A method for treating a viral infection in a subject comprising:

administering to a subject a synergistic amount of a composition comprising a combined extract of black currants and bilberries, wherein the virus is selected from the Paramyxoviridae family, wherein the combined extract of black currants and bilberries has an anthocyanin content of 29.7% by weight of the extract, wherein the combined extract of black currants and bilberries comprises a relative anthocyanin content of:

33.0% of 3-O-b-rutinoside, 3-O-b-glucosides, 3-O-b-galactosides, and 3-O-b-arabinosides of cyanidin, 58.0% of 3-O-b-rutinoside, 3-O-b-glucosides, 3-O-b-galactosides, and 3-O-b-arabinosides of delphinidin, 2.5% of 3-O-b-glucosides, 3-O-b-galactosides, and 3-O-b-arabinosides of petunidin, 2.5% of 3-O-b-glucosides, 3-O-b-galactosides, and 3-O-b-arabinosides of peonidin, and 3.0% of 3-O-b-glucosides, 3-O-b-galactosides, and 3-O-b-arabinosides of malvidin, wherein the extracts of black currant and bilberries are in a weight ratio of 1:1.

2. The method of claim 1, wherein the black currants are a fruit of *Ribes nigrum* and/or the bilberries are fruit of *Vaccinium myrtillus*.

3. The method of claim 1, wherein the extract is from the pomaces of black currants and bilberries.

4. The method of claim 1, wherein the combined extract is an alcohol extract.

5. The method of claim 1, wherein the combined extract is prepared by a process comprising the steps of extraction of black currants and bilberries, purification via chromatography, mixing of the extract(s) with water and spray-drying the mixture.

6. The method of claim 1, wherein the virus is measles virus.

7. The method of claim 1, wherein the composition is administered to the subject in 1 to 10 oral dosages of at least 80 mg anthocyanins each per day.

8. The method of claim 1, wherein the composition is configured to be administered to the subject, reaching a concentration in a target compartment of at least 30 μg/mL.

9. The method of claim 1, wherein the subject is a human.

10. The method of claim 1, wherein the subject is pregnant or younger than 15 months.

11. The method of claim 1, wherein the composition is suitable inhibiting CD150 function in the subject.

12. The method of claim 1, wherein the composition is suitable to reduce antigen-specific T cell proliferation and interferon-γ production.

13. The method of claim 1 where the composition is administered to the nasal, oral, or throat mucosal surface of the subject by A nebulizer.

* * * * *